United States Patent [19]

Vogler

[11] Patent Number: 4,748,124
[45] Date of Patent: May 31, 1988

[54] COMPARTMENTALIZED CELL-CULTURE DEVICE AND METHOD

[75] Inventor: Erwin A. Vogler, Wilmington, Del.

[73] Assignee: E. I. Du Pont de Nemours and Company, Wilmington, Del.

[21] Appl. No.: 666,617

[22] Filed: Oct. 30, 1984

[51] Int. Cl.[4] .......................... C12N 5/00; C12M 3/00
[52] U.S. Cl. .............................. 435/240.241; 435/285; 435/818
[58] Field of Search ............... 435/240, 285, 813, 818, 435/240.241

[56] References Cited

U.S. PATENT DOCUMENTS

| 3,275,528 | 9/1966 | Ainis | 435/240 |
|---|---|---|---|
| 3,821,087 | 6/1974 | Knazek et al. | 435/285 |
| 3,997,396 | 12/1976 | Delente | 435/240 |
| 4,296,205 | 10/1981 | Verma | 435/240 |
| 4,308,351 | 12/1981 | Leighton et al. | 435/284 |
| 4,332,906 | 6/1982 | Taylor | 435/291 |
| 4,440,853 | 4/1984 | Michaels et al. | 435/41 |
| 4,661,455 | 4/1987 | Hubbard | 435/285 |

FOREIGN PATENT DOCUMENTS 3105861 7/1982 Fed. Rep. of Germany ...... 435/240

OTHER PUBLICATIONS

Hawley, Condensed Chemical Dictionary, 1971, pp. 474 and 841.
Dexter, T. M., "Cell Interactions in Vitro", Clinics in Haematology 8, pp.453–568, (1979).
Rose, C. G., "Cytopathophysiology of Tissue Cultures Growing Under Cellophane Membranes", International Review of Experimental Pathology, Richter, G. W. E. Epstein, M.A., EDS., vol. 5, pp. 111, 115 and 160–178, (1966).
Marbrook J., "Primary Immune Response in Cultures of Spleen Cells". The Lancet, 2, 1279–1281, (1967).

Primary Examiner—John E. Tarcza

[57] ABSTRACT

A closed, cell culture device constructed using a first and second sheet of gas permeable, liquid-impermeable material. A third sheet of a material selectively permeable to a class of molecules sandwiched between the first and second sheets, all of the sheets being formed such that the first and third sheets define a first closed compartment and the second and third sheets define a second closed compartment, each compartment having an access port.

9 Claims, 2 Drawing Sheets

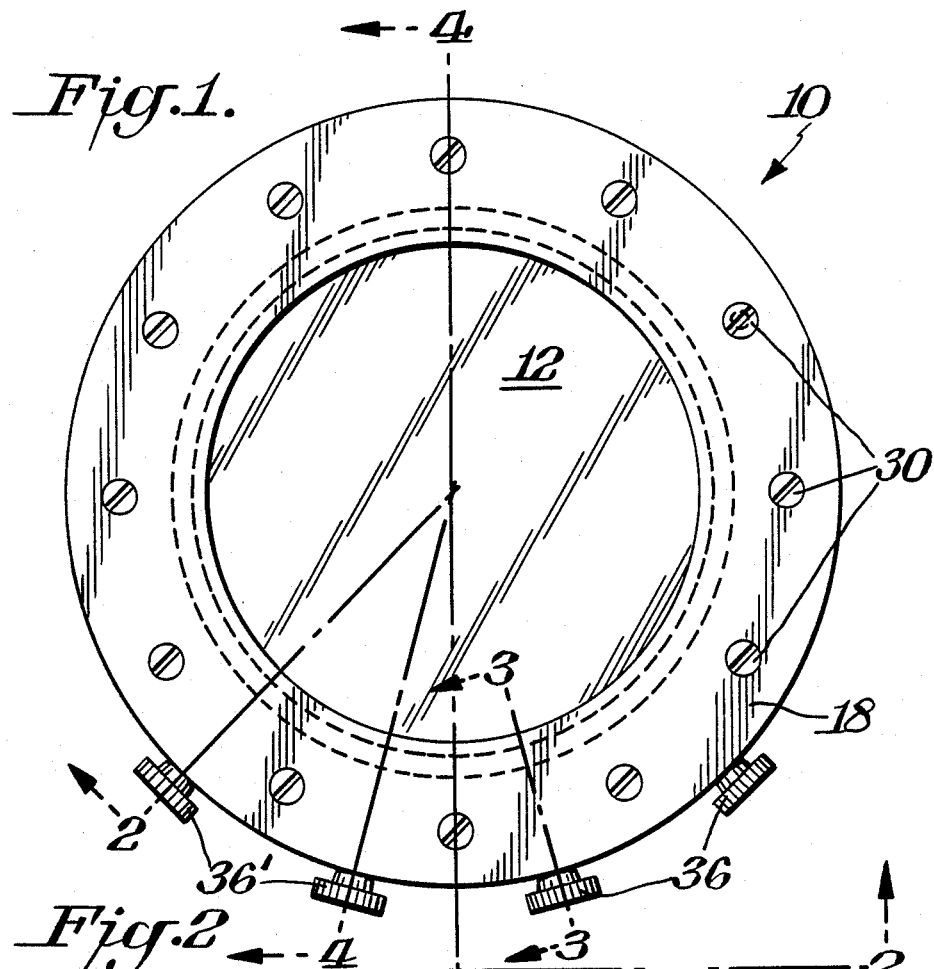
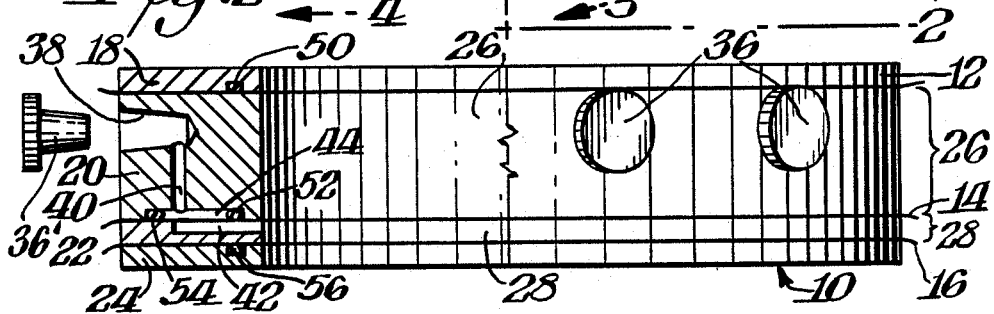
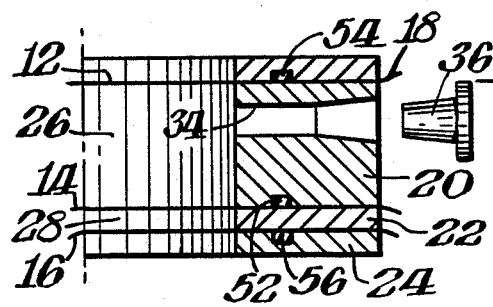
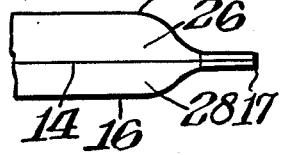

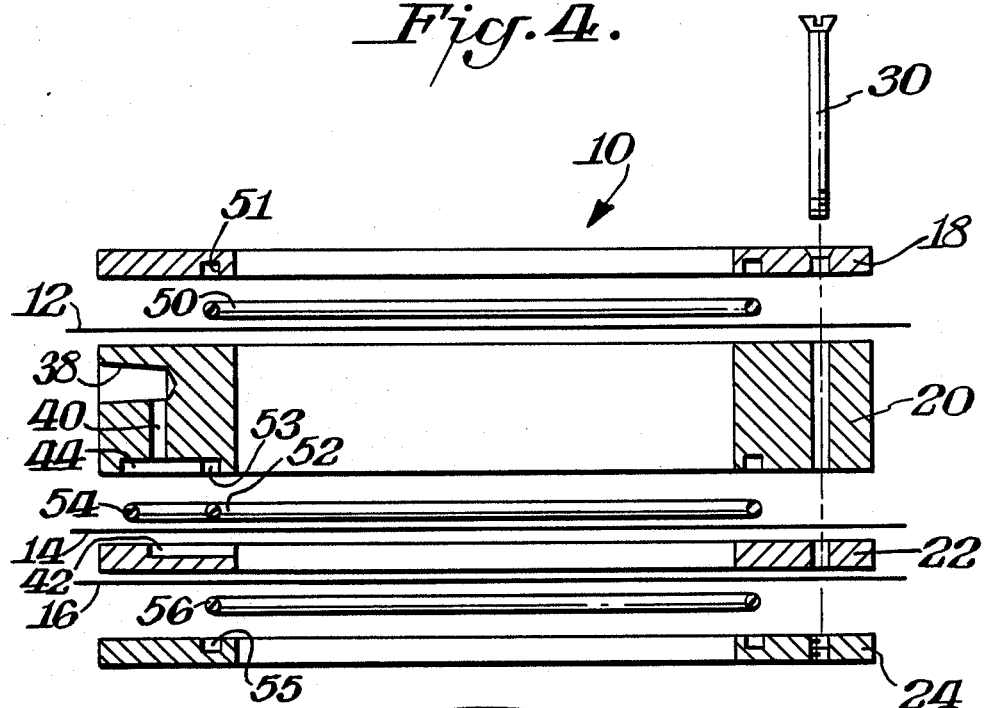
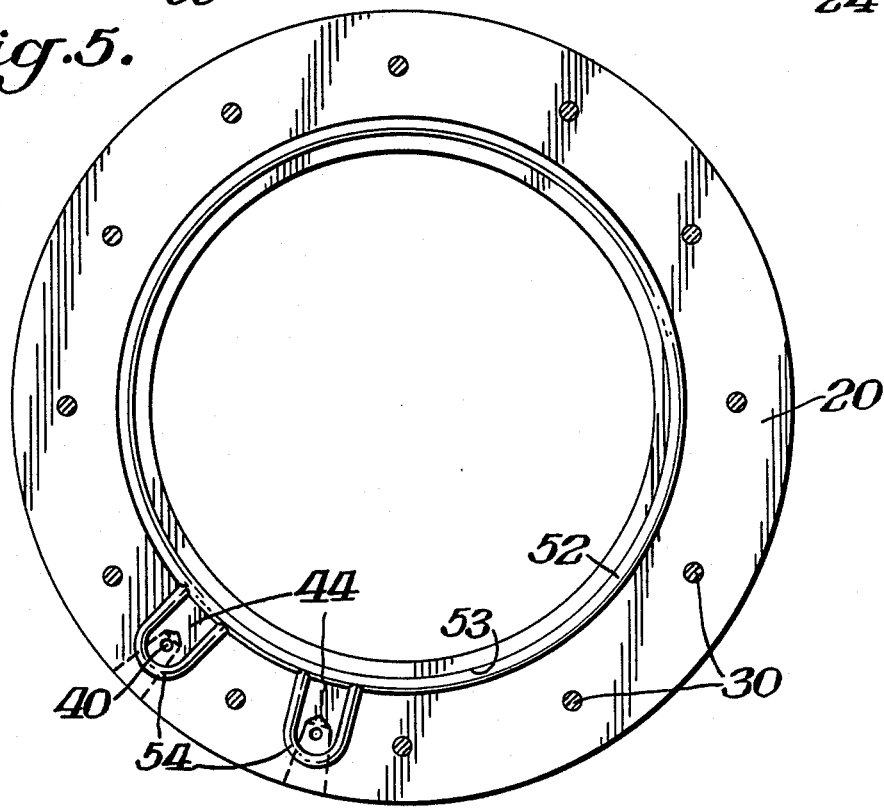

COMPARTMENTALIZED CELL-CULTURE DEVICE AND METHOD

BACKGROUND OF THE INVENTION

Mammalian cells are usually cultured in glass or plastic vessels, either in suspension or as an attached layer, completely surrounded by culture media. When nutrients are depleted or metabolic waste products accumulate, spent growth media is exchanged for fresh to sustain the culture (feeding, see Dexter, T. M., "Cell Interactions in Vitro", Clinics in Haematology, 8, 453–568 [1979]). Consequently, cells experience periodic shifts in nutrient concentrations ranging from feast (fresh media) to famine (spent media) during the course of a culture period which can last several days to a few weeks. Likewise, pericellular pH varies with a refeeding schedule because fresh media is basic relative to spent due to accumulation of acidic waste products during culture. Furthermore, soluble macromolecular cell products such as attachment factors, antibodies, and hormones (termed extracellular material or ECM; Wilde, C. E., "Bull. Groupe Franc. Argiles", 15, 183 [1961]) are removed with each refeeding, potentially altering cellular biosynthetic processes.

Although these periodic perturbations of the culture environment are not detrimental for relatively short term culture, long-term culture of cells in vitro requires a stable environment and retention of ECM (see Rose, G. G., "Cytopathophysiology of Tissue Cultures Growing under Cellophane Membranes", International Review of Experimental Pathology, Richter, G. W., Eptsein, M. A. eds., Vol. 5, 111–174, Academic Press [1966].

In order to diminish these environmental fluctuations, cells and tissue have been grown under contiguous or perforated sheets of cellulosic film so that at least part of the cellular milieu persists after media exchanges (for a review of the subject see Rose, G. G., ibid). Moreover, putative low molecular weight inhibitors and metabolic waste products can dialyze out of cell growth space. Although this method is an advancement in long-term culturing of attached cells or tissue, refeeding is still required and perturbations in cellular environment not totally avoided. Furthermore, the method is not applicable to suspension cells such as hybridoma lines because loose cells are not retained under unbounded edges of the cellulose membrane overlayer.

Simultaneous cell growth with continuous dialysis was developed by Marbrook (Marbrook, J., "Primary Immune Response in Cultures of Spleen Cells". The Lancet, 2, 1279–1281 [1967]). In this case two concentric chambers are separated by a dialysis membrane. The inner-growth chamber is partially submerged in the outer-chamber dialysis solution of larger volume. Cells are grown directly on the dialysis membrane within the inner-chamber and are continuously bathed in nutrients passing through the membrane from the outer-chamber reservoir. Disadvantages of this system include clogging of the dialysis membrane with cell mass, cellular debris, and ECM.

U.S. Pat. No. 4,296,205, issued Oct. 20, 1981 to Verma, D. S. describes the improvement over the Marbrook system of introducing a tissue-culture shelf held above the dialysis membrane to help prevent clogging and problems associated therewith. Fluid communication with the dialysis membrane and, ultimately, with a media reservoir is through perforations in the culture shelf. Although attached cells or tissue remain on the culture shelf, unattached cells and cellular debris, can become suspended and pass through tissue-culture-shelf perforations and clog or otherwise reduce critical membrane performance. Consequently, culture of suspension cells is not possible. Furthermore, during long-term culture, soluble ECM can crystallize into variously sized particles (termed biologic crystals and particles or BCP by Rose, G. G., ibid) onto or into the membrane, further compromising performance. Other difficulties with the Verma method include inability to adequately view cells during culture with high-power cytological phase-contrast and interference-contrast optics. Finally, equilibration of the culture media with incubator gasses, which is required to provide oxygen and carbon dioxide to the culture, occurs only through loosened flask caps. Proper ventilation is critical to maintenance of media pH because media mixes typically utilize a carbon dioxide/bicarbonate buffer system. Since the media reservoir volume is high, gas exchange through loosened caps is inadequate to rapidly equilibrate the entire media volume with the incubator atmosphere.

The art has sought a device and method that allows long-term, in vitro culture of both attached and suspension cells, simultaneously providing adequate gas ventilation, continuous supply of pH-equilibrated nutrient fluids, and the capability to microscopically view cells at any time during the course of culture. As shown herein, the disclosed invention meets these needs.

SUMMARY OF THE INVENTION

Many of these problems of the prior art are solved by a closed, cell-culture container constructed in accordance with this invention to have first and second sheets of a gas-permeable, liquid-impermeable material, a third sheet of a material selectively permeable to a class of molecules sandwiched between the first and second sheets, all of the sheets being formed such that the first and third sheets define a first closed compartment and the second and third sheets define a second closed compartment: each compartment having an access port or ports.

According to one embodiment of the invention, the first compartment is adapted to contain the cells to be cultured and a culture media and is located below the second compartment which is adapted to contain the culture media such that cells grow on the first sheet and do not inhibit the transfer of the class of molecules between the chambers. The first and second sheets are typically an ionomer resin and transparent for viewing microscopically. The third sheet acts as a dialysis membrane and typically is a cellulosic membrane or any other material selectively permeable to low molecular weight compounds. The membrane can be selected to retain high molecular weight proteins and immunoglobulins but allow passage of lower molecular weight compounds from the culture media reservoir.

The closed cell culture device can be constructed by sealing together all of the sheets at their edges, thereby forming the media and culture chambers accordingly. Also a closed cell culture device can be constructed using two separate peripheral support frames, a first peripheral support frame for the first and third sheets and a second peripheral support frame for the second and third sheets. All of the embodiments can include transparent sheets where the first and second sheets are ionomer resins, the third being selectively permeable to a class of molecules which can range from 8000 to 15,000 molecular weight.

With this structure a method of culturing cells comprises the steps of culturing the cells in a first compartment containing the cells to be cultured and a culture media, dialyzing the culture media simultaneously with a dialysate solution separated from the first compartment by a sheet of a material permeable to a class of molecules, and simultaneously exchanging gases in both the culture media and the dialysate solution with the surrounding environment. The gases most typically exchanged include oxygen and carbon dioxide. Also, to reduce the blockage of the third sheet by the cells, the first compartment is positioned below the second compartment.

With the invention so stated, many of the various problems identified in the prior art are solved. Long term, in vitro culture of both attached and suspension cells is possible with simultaneous provision for adequate gas ventilation, a continuous supply of pH-equilibrated nutrient fluids, and microscopic examination of cells at any time during the course of culture.

A BRIEF DESCRIPTION OF THE DRAWINGS

Other features and many of the advantages of the invention will readily become apparent from the following detailed description when considered in connection with the appended drawings in which:

FIG. 1 is a top plan view of the culture container constructed in accordance with this invention;

FIG. 2 is a cross-sectional, side elevation view of the culture container taken along the sectional lines 2—2 of FIG. 1;

FIG. 3 is a cross-section view of the culture container taken the section lines 3—3 of FIG. 1;

FIG. 4 is an exploded cross-sectional, front elevation view taken along the section line 4—4 of FIG. 1;

FIG. 5 is a bottom plan view of the culture media chamber; and

FIG. 6 is a fragmentary cross-sectional, side elevation view of an edge sealed culture container.

DETAILED DESCRIPTION OF THE PREFERRED EMBODIMENT

A closed cell culture chamber 10 constructed in accordance with this invention is best seen in FIGS. 1 and 2. In these figures, a chamber 10 preferably is formed of 3 sheets 12, 14, and 16 of a thin film material that are separated and supported by four concentric rings 18, 20, 22 and 24. The inner and outer diameters of the concentric rings in the preferred embodiment are dimensional identically defining a cylindrically shaped, upright pipe-like apparatus in its assembled form. In its assembled form, the closed cell culture chamber 10 defines two separate compartments a media reservoir compartment 26 and a growth chamber 28 used for the culturing of cells and the like. The culture chamber 10 is retained in a compressed state by a plurality of screws 30 which are evenly spaced about the circumference of the rings and hold the culture chamber 10 tightly together in a sandwich type array. Liquid-tight peripheral seals are maintained by four rubber O-rings 50, 52, 54, and 56 which are located between selected ring interfaces.

The media reservoir compartment 26 which sits alone above the growth chamber 28 is defined by ring 20 which represents a circumferential wall surrounding the reservoir and is typically ten centimeters in diameter with a wall thickness of approximately two centimeters and an axial thickness of one centimeter. Both the top and bottom surfaces of ring 20 are typically smooth and flat. The top surface of ring 20 provides for the sealing surface for both film 12 and O-ring seal 50. The bottom of ring 20 is also smooth and flat but contains a circumfertical groove 53 to retain an O-ring seal 52 as best seen in FIGS. 4 and 5. Seal 52 contacts two additional seals 54 which are located about the perimeter of inoculant cavities 44 which will be discussed later in more detail.

The upper surface of the media reservoir chamber 26 is sealed by way of a gas-permeable, liquid impermeable film 12 which in its preferred form is an ionomer resin which is optically clear and non-toxic to cells. Suitable non-ionomeric resins such as poly-carbonates, polystyrenes or polyfluorinated polymers can be used. The bottom portion of the media reservoir compartment 26 comes in contact with a dialysis membrane 14 which is sealed against the bottom surface of ring 20. The dialysis membrane 14 is selectively permeable to a class of molecules as will be described and in its preferred form is cellulosic in nature. Other suitable porous organic polymers can be used depending upon the desired application. This media reservoir compartment 26, defined by films 12 and 14 and ring 20 is accessible by way of a media access port 34 which extends completely through the wall of ring 20 at two locations as best seen in FIGS. 3 and 4. Tapered plugs 36 are used to retain the liquid media once the reservoir has been filled and are typically press fitted into media access port 34.

The growth chamber 28 which rests below the media reservoir compartment 26 is defined by ring 22 which represent a circumferential wall surrounding the growth chamber 28 and is typically ten centimeters in diameter with a wall thickness of approximately two centimeters and an axial thickness of six tenths of a centimeter. This smaller axial thickness forms a chamber having a smaller volume than the media reservoir compartment 26. Both the top and bottom surfaces of ring 22 are typically smooth and flat providing for a leak free sealing surface once in contact with films 14 and 16 and O-rings 52, 54 and 56 as best seen in FIG. 4. The upper portion of the growth chamber 28 is formed by the dialysis membrane 14 which, as previously mentioned, also acts as the bottom surface of the media reservoir compartment 26. The lower portion of the growth chamber 28 is formed by way of a gas-permeable, liquid-impermeable film 16 which preferably is identical to that of film 12 used in the media reservoir compartment 26.

Access to the growth chamber from outside the internally defined growth chamber 28 is provided by two radially-spaced inoculant access ports 38 as best seen in FIGS. 1, 2, and 4. The inoculant access port 38 radially extends to the approximate midpoint of the ring wall 20 where it communicates with a vertically disposed channel 40 which is bored 90° relative to the inoculant access port 38. The vertically disposed channel 40 communicates with the inoculant cavity 44, which as previously noted, is sealed about its parameter by way of two O-ring seals 54 and 52, as best seen in FIG. 5, which are joined at their interface by way of an adhesive such as "Eastman 910" which is commercially available. The inoculant cavity 44 in turn communicates through the film 14 by way of a cutout in the dialysis membrane 14 which is identical in shape to that of the inoculant cavity 44 to allow for an uninterrupted flow path to a radial channel 42. The radial channel 42 is formed in the top surface of ring 22 and is located midway across the width of the ring and extends toward the center of the ring to provide an open channel for inoculant passage toward the cell growth compartment. The culture chamber 10 contains two such inoculant access ports 38 spaced radially apart as best seen in FIG. 1. Tapered plugs 36' are used to retain the inoculant once the reservoir has been filled and are typically press fitted into inoculant access ports 38. Other known sealing and access methods may be used as desired. These include valves systems and the like.

FIG. 4 illustrates the culture chamber 10 in an exploded view. The chamber is assembled by first inserting each of the O-rings into their respective O-ring grooves. O-ring 50 is inserted into groove 51; in like manner, O-ring seals 52 and 56 are inserted into grooves 53 of ring 20 and 55 of ring 24. The cavity seal 54 is then positioned along the perimeter of the inoculant cavity 44 such that the ends of the seal come into direct contact with O-ring seal 52. The four rings 18, 10, 22 and 24 are then positioned in concentric alignment as depicted in FIG. 4. Film 12 is then positioned between rings 18 and 20. Dialysis membrane 14 is then positioned between rings 20 and 22 and then film 16 is positioned between rings 22 and 24. The rings are then put into compression by attachment screws 30.

There is no restriction on the size or shape of either the growth chamber 28 or the media reservoir compartment 26. However, it is recommended that the volume of the media reservoir compartment 26 exceed that of the growth chamber 28 by at least a factor of two, so that cells can be sustained without refeeding over the entire culture period. The volume of growth chamber 28 need only be sufficient in size to permit cell growth and liquid access, yielding typical media reservoir volume to growth chamber volumes 26 in the ratios of 6:1. Volume ratios, in turn, determines rings 18 and 24 thicknesses, which are typically seven tenths of a centimeter. Rings 20 and 22 can be fabricated from substances non-toxic to cells such as polystyrene, polycarbonate, or any other suitable plastic or non-plastic material that is compatible with the incubator environment. Rings 18 and 24 do not directly contact the cell-growth space or media reservoir and need not be specifically compatible with cells or biological material. The dimensions of rings 18 and 24 are not critical but should not exceed working distances of the optical systems employed in microscopes used to examine cells. Typically, three tenths of a centimeter is adequate.

In an alternative embodiment of the invention, the closed cell structure may be formed of sheets that are edge-sealed together at 17 as seen in FIG. 6, wherein the structure defines the two separate compartments 26, 28. Suitable access ports are formed in the edge seal to each chamber by sealing tubing in the edge seal. In still other alternatives, the periphery of the sheets defining the assembly, may be secured together by any suitable means such as ring clamps. In another embodiment a closed, cell culture device may include a first peripheral support frame for the first and third sheets and a second peripheral support frame for the second and third sheets.

All embodiments may include transparent sheets for use in microscopic examination and contain a dialyzing membrane which is selectable to a class of molecules depending upon application. For example, dialysis membranes which retain molecules with molecular weights greater than 15,000 are useful in retaining high-molecular weight proteins such as immunoglobulins, but allow passage of lower molecular weight compounds to and from the media reservoir. Dialysis membranes which retain molecules whose molecular weight is less than 8000, retain hormones, antigens, etc., as well as high molecular weight compounds.

In operation, the four tapered plugs 36 and 36' are removed from the culture chamber 10. The cell-growth media, which will be described in further detail in the examples, is aspirated into a syringe whose volume is representative of the media reservoir compartment 26 volume. The syringe is docked into one of the media access ports 34 and dispensed accordingly until the media reservoir compartment 26 is filled. Once this step is completed, both media access ports 34 are sealed via tapered plugs 36 which provide a leak-free seal. The inoculant is now aspirated using a syringe whose volume is suitable to deliver a predetermined specimen into the growth chamber 28. In similar fashion, the syringe tip is docked into the inoculant access port 38 and dispensed accordingly. Once filled, the ports are sealed via tapered plugs 36' to retain the culture media within. This now completes the inoculation of the growth chamber and filling of media reservoir. Depending upon the application, the culture chamber 10 can be housed in an incubator for processing.

During processing, cells are cultured in the growth chamber 28. The dialysis membrane 14, being permeable to a specific class of molecules, will permit dialysis or culture media against the dialysate solution in the media reservoir. Gas exchange occurs through films 12 and 16 and are typically oxygen and carbon dioxide, but depending on application can vary to need. Consequently, cells are continuously fed with pH-equilibrated nutrient media permeating the membrane while, at the same time, putative low molecular weight metabolic waste products are held a low pericellular concentration by equilibrating with the media reservoir volume. The culture is ventilated and equilibrated with the incubator gaseous environment through optically clear, gas-permeable, liquid-impermeable film bounding cell-growth and media reservoir chambers. The net effect is a stable culture environment without periodic perturbations associated with a conventional culture-refeeding schedule. Throughout the entire culture period, cells can be viewed using high-power cytological phase-contrast and interference-contrast microscopes commonly employed in cell-culture laboratories. There is little or no clogging of the films which often occurs in the prior art.

The apparatus and method of this invention allows long-term, in vitro culture of both attached and suspension cells, simultaneously providing adequate gas ventilation, continuous supply of pH-equilibrated nutrient fluids, and the capability of microscopically viewing cells at any time during the course of culture. As shown herein, the disclosed invention meets these needs. While the device 10 has been described as being generally cylindrical in shape with a circular cross-section, it is to be understood that it may be constructed to have other geometric shapes, such as but not limited to those having rectangular, square or other similar cross-sections.

EXAMPLE 1

The device that is shown in FIGS. 1 and 2 was assembled using 4 mil films cast from zinc-ionomer resin available from E. I. Du Pont de Nemours Co. under the trade name Surlyn ® 1702 for barriers 12 and 16. Dialysis membrane 14 was a 1.8 mil thick cellulosic membrane permeable to molecules within the molecular-weight range less than 5,000 to 8,000 available from VWR Scientific Incorporated. A 2:1 media to culture compartment volume ratio was created using 0.8 and 0.4 cm thicknesses for rings 18 and 20, respectively, with a total surface area of 22 sq. cm., yielding an 18 ml. media reservoir compartment 26 and a 9 ml. growth chamber 28. Rings 18, 20, 22, and 24 were fabricated from polymethylmethacrylate plastic. Approximately 9 ml. of media (Iscove's Modified Dulbecco's Medium containing 10% FBS, Gibco Laboratories) containing $7 \times 10^4$ MDCK cells/ml. (Medin-Darby Canine Kidney cells. American Type Culture Collection) was injected into the growth chamber 28 and 18 ml of media not containing cells was used to fill the media reservoir compartment 26. Cell attachment to the film 16 and proliferation to a confluent monolayer was documented by photomicrography. The monolayer was sustained for 27 days without media exchanges in a prolonged stationary phase reaching $4.3 \times 10^5$ cells/sq. cm. Normal and invarient morphology was observed throughout the entire stationary phase. Cells had a 14.1 $\mu$m median diameter with a standard deviation of 4.8 $\mu$m. Cells were subcultured to conventional polystyrene cultureware and had normal morphology to confluence.

By contrast, MDCK sustained for 37 days in polystyrene flasks with refeeding every 48 hours exhibited continual morphological changes throughout the culturing period including cell detachment from the substrate, formation of irregularly shaped, raised, amorphous ridges, and excessive vaccuolization. Final density achieved was $3.8 \times 10^5$ cells/sq. cm. Cells had a median diameter of 14.5 $\mu$m with a standard deviation of 12.1 $\mu$m.

EXAMPLE 2

The growth chamber 28 of a device constructed as in Example 1 was inoculated with a dilute suspension ($\sim 1 \times 10^4$ cells/ml) of immunoglobulin-secreting hydridoma cells in 9 ml. of media containing 5% FBS (Iscove's modified Dulbecco's medium for hydridomas. Whittaker M. A. Bioproducts). The media reservoir 26 was filled with 18 ml. of media containing neither serum nor cells. The culture was sustained for 33 days without media exchanges. Cells continued to secrete immunoglobulin throughout the culture period and multiplied to $1.7 \times 10^7$ cells at harvest. No immunoglobulin was detected in the media reservoir at the end of the experiment verifying the integrity and performance of the dialysis membrane.

What is claimed is:

1. A method of culturing cells comprising the steps:
   placing the cells in a first compartment with a culture medium, said first compartment composed of an upper dialysis membrane and a lower gas-permeable, liquid-impermeable sheet;
   injecting a culture medium in a second compartment above said dialysis membrane;
   permitting waste products from said cells to flow upwardly through said dialysis membrane; and
   exchanging incubator gases through said gas-permeable sheet whereby said cells grow continuously without clogging said dialysis membrane.

2. A closed dual compartment cell culture device comprising:
   two sheets of gas-permeable, liquid impermeable material disposed horizontally with one over the other to form a top sheet and a bottom sheet;
   a dialysis membrane disposed between said two sheets;
   one separating means between said membrane and said bottom sheet to form a bottom compartment adapted to contain cells to be cultured and a culture medium;
   second separating means between said membrane and said top sheet to form a top compartment adapted to contain a culture medium;
   access ports in each of said separating means to permit injection of material into said compartments;
   said dialysis membrane adapted to permit waste products to flow from said bottom compartment to said top compartment while adapted to retain macromolecules for cell growth in the bottom compartment and said gas-permeable sheets are adapted to exchange incubator atmospheric gases.

3. A device as set forth in claim 2 wherein said two sheets are composed of an ionomer resin.

4. A device as set forth in claim 2 wherein said two sheets are transparent.

5. A device as set forth in claim 2 wherein said dialysis membrane is a cellulosic membrane.

6. A device as set forth in claim 2 wherein said dialysis membrane is permeable to compounds having a molecular weight less than 8000 and impermeable to compounds having a molecular weight of 8000 and above.

7. A device as set forth in claim 2 wherein said dialysis membrane is permeable to compounds having a molecular weight less than 15,000 and impermeable to compounds having a molecular weight of 15,000 and above.

8. A device as set forth in claim 2 wherein said separating means between said sheets involves seals surrounding the edges of said sheets.

9. A device as set forth in claim 2 wherein said separating means comprises two peripheral support frames, one separating the top sheet and the dialysis membrane and a second separating the dialysis membrane and the bottom sheet.

* * * * *